United States Patent [19]
Borgman

[11] Patent Number: 6,147,102
[45] Date of Patent: Nov. 14, 2000

[54] CLONIDINE PREPARATIONS

[75] Inventor: Robert J. Borgman, Mundelein, Ill.

[73] Assignee: Curatek Pharmaceuticals Holding, Inc., Las Vegas, Nev.

[21] Appl. No.: 09/427,367

[22] Filed: Oct. 26, 1999

[51] Int. Cl.$^7$ .................. A61K 31/415; A61K 31/24; A61K 31/74
[52] U.S. Cl. .................. 514/392; 514/817; 514/944; 514/535; 514/536; 514/537; 424/78.02
[58] Field of Search .................. 514/392, 817, 514/944, 535, 536, 537; 424/78.02

[56] References Cited

U.S. PATENT DOCUMENTS

| | | | |
|---|---|---|---|
| 5,447,947 | 9/1995 | Campbell | 514/392 |
| 5,605,911 | 2/1997 | Olney et al. | 514/315 |
| 5,780,049 | 7/1998 | Deckner et al. | 424/449 |

OTHER PUBLICATIONS

Byas–Smith et al., "Transdermal clonidine compared to placebo in painful diabetic neuropathy using a two–stage 'enriched enrollment' design," *Pain*, 60, 267–274 (1995) (abstract).
Davis et al., "Topical application of clonidine relieves hyperalgesia in patients with sympathetically maintained pain," *Pain*, 47, 309–317 (1991) (abstract).
Eisenach et al., "Epidural clonidine analgesia for intractable cancer pain:phase I," *Anesthesiology*, 71, 647–552 (1989) (abstract).
Epstein et al., "Topical clonidine for orofacial pain: a pilot study," *J. Orofac. Pain*, 11, 346–352 (1997) (abstract).
Glynn et al., "A double–blind comparison between epidural morphine and epidural clonidine in patients with chronic non–cancer pain," *Pain*, 34, 123–128 (1988) (abstract).
Langley et al., "Transdermal clonidine. A preliminary review of its pharmacodynamic properties and therapeutic efficacy," *Drugs*, 35, 123–142 (1988) (abstract).
Max et al., "Association of pain relief with drug side effects in postherpetic neuralgia: a single–dose study of clonidine, codeine, ibuprofen and placebo," *Clin. Pharmacol. Ther.*, 43, 363–371 (1988) (abstract).
Mendez et al., "Epidural clonidine analgesia after cesarean section," *Anesthesiology*, 73, 848–852 (1990) (abstract).
Nakamura et al., "Peripheral analgesic action of clonidine: mediation by release of endogenous enkephalin–like substances", *Eur. J. Pharmacol.*, 146, 223–228 (1988) (abstract).
Yaksh, T.L., "Pharmacology of spinal adrenergic systems which modulate spinal nociceptive processing", *Pharmacol. Biochem. Behav.*, 22, 845–858 (1985) (abstract).
Zeigler et al., "Transdermal clonidine versus placebo in painful diabetic neuropathy," *Pain*, 48, 403–408 (1992) (abstract).

*Primary Examiner*—Theodore J. Criares
*Assistant Examiner*—Jennifer Kim
*Attorney, Agent, or Firm*—Olson & Hierl, Ltd.

[57] ABSTRACT

Sympathetically maintained peripheral neuropathic pain syndromes are relieved by topically applying, to the affected region of a patient suffering from such pain, a pain relieving amount of an aqueous gel comprising clonidine, a water-gelling amount of a pharmaceutically acceptable gelling agent and having a physiologically tolerable pH value. Pain relief was achieved with applied amounts of clonidine in the range of about 2 milligrams per day to about 6 mg per day.

25 Claims, 1 Drawing Sheet

CLONIDINE PREPARATIONS

TECHNICAL FIELD OF THE INVENTION

This invention relates to the relief of sympathetically maintained peripheral neuropathic pain syndromes, and in particular, to the use of gel compositions containing clonidine.

BACKGROUND OF THE INVENTION

Sympathetically maintained peripheral neuropathic pain syndromes of acute or chronic origin can encompass painful diabetic neuropathy (PDN), post-herpetic neuralgia (PHN), complex regional pain syndrome(CRPS) and like chronic non-malignant neuropathic pain syndromes. Patients with sympathetically maintained peripheral neuropathic pain syndromes typically have stimulus-independent (ongoing) pain and stimulus-dependent pain (hyperalgesia).

Conventional treatments for these pain syndromes include oral administration of tricyclic antidepressants, anti-epileptics, and other miscellaneous neurological agents. Some prior attempts also have been made to treat sympathetically maintained peripheral neuropathic pain syndromes with adrenergic compounds such as clonidine or phentolamine.

Clonidine, in particular, is a potent $\alpha_2$-adrenergic partial agonist used primarily for the treatment of hypertension (Jarrott et al., "Clonidine: Understanding its disposition, sites, and mechanism of action", Clin. Exp. Pharm. Physiol., 14, 471–479 (1987)). This drug stimulates $\alpha_2$-adrenoceptors in the vasomotor centers, causing a reduction of sympathetic outflow from the central nervous system. Both cardiac output and peripheral resistance are reduced resulting in a decrease in blood pressure. Higher concentrations cause a vasoconstriction by activation of postsynaptic receptors in vascular smooth muscle. However, the significant advantages of the drug are counter balanced by certain troublesome side effects including dryness of the mouth and a discouraging dizziness. Therefore, the blood concentration of clonidine must be controlled within a narrow therapeutic window.

Clonidine and related $\alpha_2$-adrenergic agonists have been reported to modify nociception in animal models. See Yaksh, T. L., "Pharmacology of spinal adrenergic systems which modulate spinal nociceptive processing", Pharmacol. Biochem. Behav., 22, 845–858 (1985); and Nakamura et al., "Peripheral analgesic action of clonidine: mediation by release of endogenous enkephalin-like substances", Eur. J. Pharmacol., 146, 223–228 (1988). In clinical studies, single doses of epidural clonidine have been reported to relieve post-operative pain (Mendez et al., "Epidural clonidine analgesia after cesarean section", Anesthesiology, 73, 848–852 (1990)), cancer pain (Eisenach et al., "Epidural clonidine analgesia for intractable cancer pain:phase I", Anesthesiology, 71, 647–552 (1989)), and pain due to arachnoiditis (Glynn et al., "A double-blind comparison between epidural morphine and epidural clonidine in patients with chronic non-cancer pain", Pain, 34, 123–128 (1988)).

In a controlled trial of single oral doses of 0.2 milligrams (mg) clonidine in 40 patients with postherpetic neuralgia, observed pain relief was greater than that produced by doses of placebo or 120 mg codeine, but the modest analgesia was accompanied by troublesome levels of sedation and dizziness at the time of peak clonidine levels. (Max et al., "Association of pain relief with drug side effects in postherpetic neuralgia: a single-dose study of clonidine, codeine, ibuprofen and placebo", Clin. Pharmacol. Ther., 43, 363–371 (1988)).

Some attempts have been made to relieve pain, allodynia and hyperalgesia employing transdermal patches containing clonidine, but the effects achieved were restricted to the skin underlying the patch. Hyperalgesia is defined as a leftward shift of the stimulus-response function, such that a lowering of pain threshold or an increase in pain to suprathreshold stimuli or both is observed. The decrease in pain threshold to mechanical or thermal stimuli may be such that lightly stroking the skin evokes pain, a phenomenon sometimes referred to as allodynia.

For example, Davis et al., in "Topical application of clonidine relieves hyperalgesia in patients with sympathetically maintained pain," Pain, 47, 309–318 (1991) reported that delivery of clonidine by transdermal patch relieved sympathetically maintained hyperalgesia in the skin adjacent to the patch Likewise, Campbell in U.S. Pat. No. 5,447,947 describes hyperalgesia relief with transdermal patches delivering a systemic dose of 0.2 mg and 0.3 mg of clonidine/day (i.e., 30 micrograms/square centimeter patch/day), but the zone of relief was generally limited to the skin area at or adjacent the patch site along with some skin irritation surrounding the patch site and side effects were noted.

In a placebo-controlled cross-over pain trial in patients with painful diabetic neuropathy utilizing clonidine transdermal patches no statistically significant differences between treatments were observed by Zeigler et al., "Transdermal clonidine versus placebo in painful diabetic neuropathy", Pain, 48, 403–408 (1992). In a follow-up placebo controlled pain study in similar patients with painful diabetic neuropathy, transdermal clonidine patches were evaluated using a two-stage enriched enrollment design by Byas-Smith et al., "Transdermal clonidine compared to placebo in painful diabetic neuropathy using a two-stage enriched enrollment' design", Pain, 60, 267–274 (1995). Only twelve of forty-one patients (29%) who completed the initial course of treatment were considered clonidine responders. These twelve clonidine responders were then rechallenged in a second placebo controlled study which used the highest dosage available with the transdermal patch system. The pain reduction relative to placebo tended to be modest although statistically significant ($p<0.015$).

Based on the foregoing attempts it would appear that relatively higher concentrations of clonidine are needed at the painful site. Unfortunately, with the dosage forms utilized, higher doses cannot be given without accompanying undesirable systemic side effects. While clonidine is a desirable potent analgesic drug, it has a narrow therapeutic index.

A desirable treatment for sympathetically maintained peripheral neuropathic pain syndromes, therefore, would be a topical composition of clonidine that could be spread over the entire painful area to deliver targeted high concentrations to the painful site yet affording minimum systemic concentrations.

The present gel composition answers the need for delivering therapeutically effective amounts of clonidine directly to the affected region of patients suffering sympathetically maintained peripheral neuropathic pain syndromes while avoiding undesirable systemic effects.

SUMMARY OF THE INVENTION

Topical aqueous gel compositions containing clonidine are suitable for relieving sympathetically maintained peripheral neuropathic pain. Sympathetically maintained peripheral neuropathic pain is relieved by topically applying, to the affected region of a patient suffering from such pain, a pain relieving amount of an aqueous gel comprising clonidine, and a pharmaceutically acceptable water-gelling agent.

The aqueous gel has a physiologically tolerable pH value. The gels contain clonidine present in an amount in the range of about 0.01 to about 0.5 weight percent based on the weight of the gel. A preferred gel contains clonidine in an amount in the range of about 0.01 to about 0.075 weight percent, based on the weight of the gel.

Preferably, the gelling agent is a carbomer, a glycerin polyacrylate, or a mixture thereof. The gelling agent can provide moisturizing, skin-humectant benefits as well. A preservative, a topical anesthetic and a supplemental skin-humectant also can be present.

Pain relief was achieved with topically applied amounts of clonidine at dosages preferably in the range of about 2 milligrams per day to about 6 milligrams per day.

Advantageously, the topical clonidine gels can be applied and spread over the entire affected region of a patient suffering from a sympathetically maintained peripheral neuropathic pain syndrome, such as from diabetic neuropathy, postherpetic neuralgia and like peripheral neuropathic pain syndromes. In addition, these topical clonidine gels are capable of delivering relatively high amounts of clonidine directly to the affected region where required while limiting the total amount of clonidine going into the general circulation to levels that avoid or at least minimize systemic adverse effects.

DESCRIPTION OF THE PREFERRED EMBODIMENT

Figure 1:
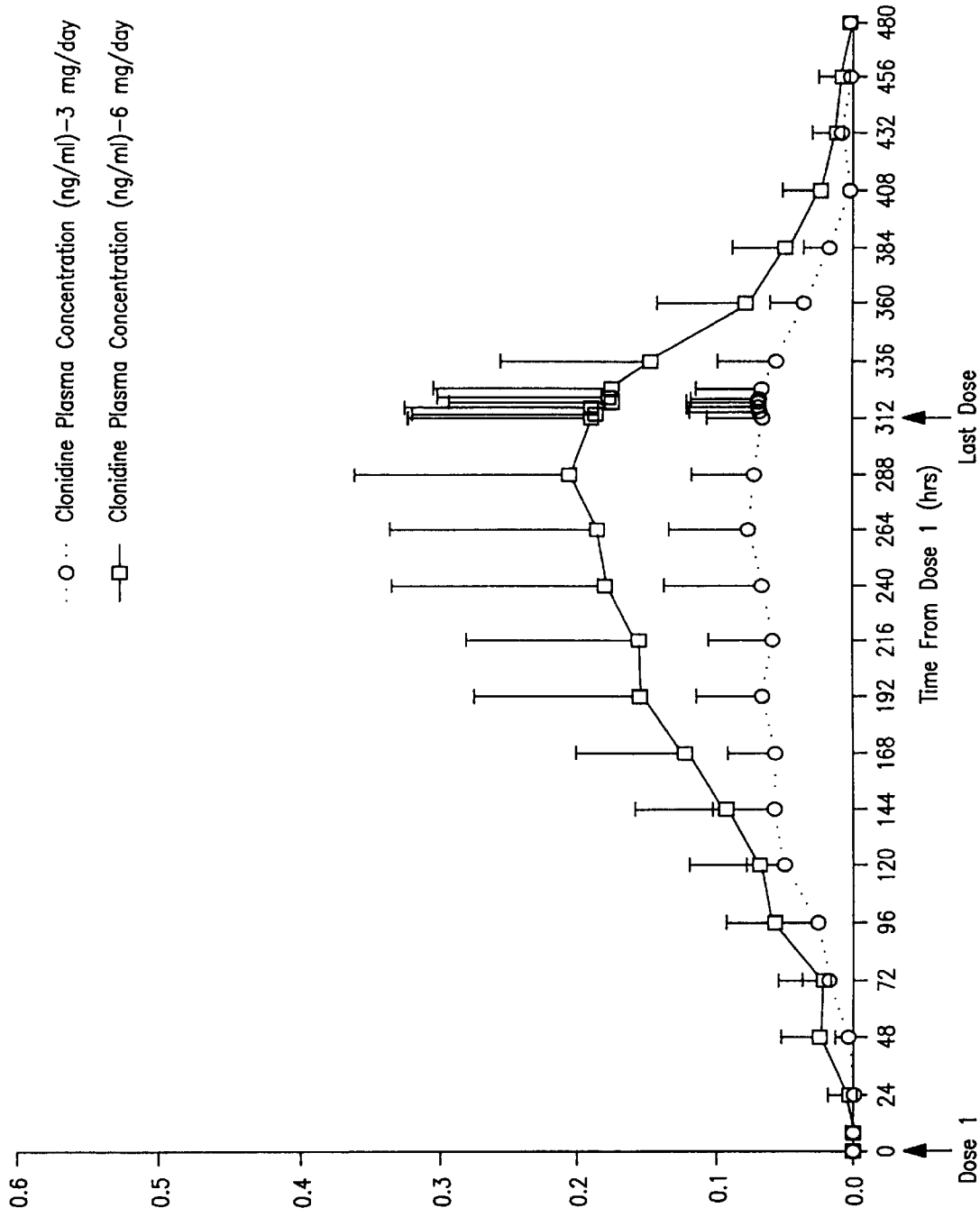
FIG. 1 is a graph illustrating clonidine plasma concentrations in nanograms/milliliter following regimens of topical applications of aqueous gels containing 0.1% clonidine applied in unit doses which provide total daily dosage amounts of about 3 milligrams and about 6 milligrams of clonidine/day in accordance with the present invention.

The term "clonidine" as used herein refers to N-(2,6-dichlorophenyl)-4,5-dihydro-1H-imidazol-2-amine and includes the pharmaceutically acceptable salts thereof, e.g., the hydrochloride salt thereof.

The term "pharmaceutically acceptable" as used herein means that the ingredient is not a known irritant or sensitizer of human skin and has not been prohibited or restricted from use in topical skin products by the Food and Drug Administration.

The term "gel" as used herein refers to viscous, aqueous compositions preferably containing at least about 85 weight percent water on a total gel weight basis and a sufficient amount of pharmaceutically acceptable water-gelling agent to produce a viscoelastic composition having a thixotropic viscosity.

Topical gels containing clonidine were prepared that provided increased pain relief for more patients suffering from sympathetically maintained peripheral neuropathic pain syndromes by delivering clonidine directly to the entire affected region employing concentrations of clonidine greater than those of prior art attempts.

The following factors are significant in the development of topical gel formulations of clonidine for treating sympathetically maintained peripheral neuropathic pain syndromes:

1. The region of pain varies with the condition treated, e.g., painful diabetic neuropathy may involve only one foot or both feet, or the feet and hands, or the feet, calves and hands. Therefore, the total dose given will vary depending on the region of involvement and the corresponding amount of gel required to cover the affected regions. If too much clonidine is applied, systemic concentrations of clonidine rise to levels appropriate for antihypertensive therapy and thus cause treatment limiting side effects. The side effects in normotensive people can include dizziness, sedation, drymouth, bradycardia, and hypotension. Therefore, the present formulations and delivery methods balance the amount applied (concentration and total amount) with the size of the region to be treated with avoidance of high systemic clonidine blood concentrations.

2. Another factor is the variability of each individual's perception of pain and response to treatment. A sufficiently high dose must be available to those patients who have higher pain tolerance thresholds. These patients are not likely to respond to allowable systemic concentrations from oral or patch technology administration.

3. An appropriate gel vehicle is necessary for ease of drug administration, drug solubility and stability, as well as drug concentration and pH value to provide the necessary non-ionized concentration of drug with the requisite thermodynamic activity for effective topical delivery and bioavailability.

An effective aqueous topical clonidine gel composition embodying the present invention comprises the following constituents:

| Ingredient | Conc. (% w/w) |
|---|---|
| Clonidine HCl | 0.01 to 0.5 |
| Water-gelling agent | 0.1 to 2 |
| Preservative | 0.1 to 2 |
| Topical anaesthetic | zero to 5 |
| Skin-humectant | zero to 5 |
| pH adjusting agent to final pH 7.5 to 8.5 | q.s. |
| Purified Water USP | to 100% q.s. |

Clonidine is employed in a therapeutically effective amount, preferably in the form of clonidine base. The actual concentration of clonidine may vary, depending on the nature and degree of the pain syndromes being treated and whether the drug is being administered for therapeutic or prophylactic purposes. Preferably the total daily amount of clonidine absorbed by the patient in need of treatment from doses of topically applied gel is not more than about 0.2 nanograms/milliliter, based on blood plasma concentrations to avoid undesirable systemic effects.

The present topical clonidine gel contains at least about 0.01 weight percent clonidine, based on the total weight of the gel. Preferably clonidine is present in an amount in the range of about 0.01 to about 0.5 weight percent, more preferably in the range of about 0.01 to about 0.25 weight percent, and most preferably in the range of about 0.01 to about 0.075 weight percent, based on the weight of the gel.

Pharmaceutically acceptable water-gelling agents preferably are carbomers, glyceryl polyacrylates, and combinations thereof. Carbomers are a series of water-gelling homopolymers of acrylic acid crosslinked with an allyl ether of pentaerythritol, an allyl ether of sucrose, or an allyl ether of propylene available in various viscosity grades sold under the trademark designation CARBOPOL® by B. F. Goodrich Company, Cleveland, OH. Particularly preferred is CARBOPOL® 980. Glyceryl polyacrylates are esters of glycerine and polyacrylic acid available in various viscosity grades sold as an aqueous jelly under the trademark designation, HISPAGEL, by Hispano Quimica S. A., Barcelona, Spain. When a combination of a carbomer and a glyceryl polyacrylate is employed as the water-gelling agent, the glyceryl polyacrylate preferably is a minor portion of the total amount of water-gelling agent used. Glyceryl polyacrylate, if present, also contributes a skin moisturizing effect.

The water-gelling agent imparts a desirable viscous, thixotropic consistency to the topical gel when mixed with clonidine and water. Preferably the gel contains at least about 85 percent by weight water, more preferably 95 percent by weight water, based on the total weight of the gel. The amount of gelling agent can vary depending on degree of gel viscosity desired. Preferably the amount of water-gelling agent is in the range of about 0.1 to about 2 weight percent, more preferably of about 0.5 to about 1.5 weight percent, and most preferably not more than about 1 weight percent, based on the total weight of the gel.

It is known that the skin of patients affected with sympathetically maintained peripheral neuropathic pain syndromes, and especially diabetic patients affected with diabetic neuropathy, tends to be dry. Conventionally, such patients typically apply skin-moisturizing products to their skin. In the topical gels of the present invention, the water-gelling agent may also provide some skin-humectant benefits by maintaining moisture at the affected site, without interfering with the pain relieving efficacy of the clonidine, thereby minimizing the need for applying additional skin-moisturizing products.

Optionally, supplemental, water-soluble, skin-humectant adjuvants that have skin-moisturizing properties or anti-irritant properties also can be included, so long as they do not interfere with the pain relieving efficacy of the clonidine. Example skin-humectants include but are not limited to polyhydric alcohols having two to six carbon atoms per molecule, such as glycerin, sorbitol, propylene glycol, and polyglycerols having two to ten glycerin units and the like. The amount of skin-humectant, when present, can vary in the range of about 0.1 to about 5 weight percent, preferably of about 0.5 to about 3 weight percent, based on the total weight of gel.

Aqueous solutions of carbomer polymers form gels when neutralized with a base. Water-soluble bases which have been used to promote gelling of carbomers, such as the CARBOPOL® series of polymers include, for example, inorganic bases, such as an aqueous solution of NaOH, and organic bases, such as alkylamines, dialkylamines, trialkylamines, alkanolamines, dialkanolamines, trialkanolamines having one to four carbon atoms in the alkyl or alkanol chain and the like. A presently preferred inorganic base is NaOH, and a preferred organic base is monoethanolamine or triethanolamine.

The pharmaceutically effective component of the gel composition, clonidine hydrochloride, is itself acidic in aqueous solution, so some base neutralization is typically required to promote gelling of the carbomer. At a pH value of about 8, the topical clonidine gel may comprise clonidine in both the hydrochloride form and free base form.

Preservatives may be incorporated in an amount effective for inhibiting growth of microbes, such as bacteria, yeast and molds, in the gel during storage. Any conventional preservative against microbial contamination of the product can be employed so long as it is pharmaceutically acceptable, is unreactive with clonidine, and is non-irritating or non-sensitizing to human skin. Preferred preservatives are antimicrobial aromatic alcohols, such as benzyl alcohol, phenoxyethanol, phenethyl alcohol, and the like, and esters of parahydroxybenzoic acid commonly referred to as paraben compounds, such as methyl, ethyl, propyl, and butyl esters of parahydroxybenzoic acid and the like and mixtures thereof, but are not limited thereto. Particularly preferred are benzyl alcohol and phenoxyethanol. The amount of preservative is preferably not more than about two weight percent, based on the total weight of the gel.

Optionally, a topical, preferably water-soluble, anaesthetic agent, such as lidocaine and the like, can be included. If present, the amount of anaesthetic agent can vary in the range of about 0.1 to about 5 weight percent.

The pH value of the gel can be in a physiologically tolerable range of about 4 to about 9, preferably of about 6 to about 8.5, most preferably of about 7.5 to about 8.25. The term "physiologically tolerable" as used herein refers to a gel medium that is non-irritating to human skin.

Any suitable method of adjusting the pH value of the aqueous gel may be used. Preferably, sodium hydroxide (NaOH) is added as a concentrated aqueous (10 to 20 weight percent) solution to the aqueous vehicle containing the water-gelling agent to bring the final pH value to the desired level. When carbomer is employed, the gel viscosity typically increases as the carbomer in the gel is neutralized with base, e.g., with NaOH or triethanolamine, following the recommendations of the carbomer manufacturer for dissolving and neutralizing the carbomer.

The ingredients listed above may be combined in any order and manner that produces a one-phase aqueous gel of the desired consistency and pH value with clonidine dissolved therein and substantially evenly distributed or dispersed throughout.

One preferred method of preparing such a gel involves preparation of an aqueous solution of clonidine with a portion of the water content and then dissolving the gelling agent therein. The preservative and any remaining optional ingredients (i.e., topical anaesthetic and skin-humectant adjuvant) can be subsequently included and then the pH of the mixture is adjusted by adding the pH adjusting agent as needed to simultaneously form a gel having the desired viscosity and pH value.

Another method of preparing such gel compositions involves preparation of an aqueous solution of the water-gelling agent., which hereinbelow will be called "Part A", by dissolving the gelling agent in a portion of the water content according to the manufacturer's directions. Preferably the gelling agent is dissolved in purified water, such as distilled water. A separate "Part B" aqueous solution can be prepared comprising the clonidine, and, if present, the preservative, topical anaesthetic agent, and skin-humectant adjuvant. Parts A and B are then combined, and the pH of the mixture is adjusted by adding the pH adjusting agent as needed to simultaneously form a gel having the desired viscosity and pH value.

Alternatively, the clonidine, preservative and remaining optional ingredients (i.e., topical anaesthetic and skin-humectant adjuvant) can be included separately or together in either Part A or Part B.

The gel is preferably packaged in any suitable container indicating use and from which it can be either extruded or dispensed, such as a squeezable tube, syringe, or the like, directly onto the affected region. The volume of gel so contained is conveniently and preferably selected to constitute a predetermined unit dose, such as a single daily dose, or two or more daily doses, or the like, to facilitate administration of a desired controlled dose to the painful affected region of a patient. The package can be initially sealed and be opened at the time of use. If more than a single dose is present, the package is preferably resealable by a suitable closure means.

A preferred package is a container, such as a bottle and the like, fitted with a pump dispenser that delivers a metered predetermined standardized unit dose on actuation.

Another presently preferred package is a moisture-impermeable packet containing an intended single unit dose. The packet can be initially sealed, and be opened at the time of use by tearing, cutting, or the like at a desired or planned location in the packet after which the packet is manually squeezed so that the contents are directly administratable as desired.

The quantity of clonidine contained in a unit dose ranges from about 0.05 milligram (mg) to about 3.5 mg, more preferably in the range of about 0.15 to about 0.6 mg, most preferably in the range of about 0.3 to about 0.5 mg. Such a quantity of unit doses can be administered one to four times daily, at spaced intervals in a single day and over a period of days as needed. The total daily dose thus delivered can range from about 0.1 to not more than about 6 mg clonidine.

A presently preferred administration procedure is to employ a unit dose of gel to deliver a dose of about 0.3 mg of clonidine administered one to four times daily to the affected painful region. Those skilled in the art will appreciate that the foregoing dose levels are provided illustratively, and that higher and lower dose levels can be employed without departing from the spirit and scope of the present invention.

Desirably, the topical clonidine gel of this invention can be spread over the entire affected painful region of a patient to deliver targeted high concentrations to the painful site yet afford minimum systemic concentrations. This can be accomplished with the topical gel by varying the concentration of clonidine in the gel and by varying the number of applications of gel per day to provide therapeutically effective amounts while minimizing the possibility of systemic effects. The topical clonidine gel can be applied directly to the affected region preferably by applying gel and then rubbing the gel into the skin.

Two preliminary studies were conducted to characterize the pharmacokinetics from the application of clonidine gel. In the first study a single 2 mg dose of clonidine gel was applied to the skin of normotensive volunteers and the clonidine plasma concentrations were measured utilizing Gas Chromatograph/Mass Spectrum analysis having a limit of quantitation of 0.025 nanograms/milliliter (ng/ml). With this dosage, all clonidine plasma concentrations were below the limits of quantitation. In the second study a 7.5 mg daily dose of clonidine was applied. Besides producing measurable plasma concentrations, the dose of 7.5 mg clonidine per day produced adverse events, such that the volunteers prematurely discontinued dosing for intolerable adverse events after seven days. Following the discontinuation of treatment the clonidine plasma concentrations had a calculated half life of 39–80 hours suggesting a prolonged absorption from tissue binding sites into the blood.

A third pharmacokinetic study described in Example 2 below, was conducted which compared topical daily doses of 3 mg and 6 mg clonidine and the mean plasma concentrations were found to be not more than about 0.2 nanograms/ml as shown in FIG. 1 and no side effects were observed.

It was found that topical applications of clonidine gel have particular analgesic efficacy in two sympathetically maintained peripheral neuropathic pain syndromes: postherpetic neuralgia and painful diabetic neuropathy. Pilot trials in patients with these pain syndromes showed that effective pain relief occurs over a daily dose range of about 2 mg to about 5 mg clonidine. Although clonidine doses above five mg per day were also found to be analgesic, there was no apparent beneficial increase in analgesia with the higher doses but the frequency and severity of clonidine related systemic adverse events increased.

It was found that a topical clonidine gel formulation containing 0.05 to 0.1 weight percent clonidine applied to the skin of the lower extremities, such as the foot or leg region from once a day up to three times per day affords systemic clonidine plasma concentrations below or at the lower limit of those required for antihypertensive therapy. Advantageously, these topical clonidine gels provide the necessary amount of on-site clonidine concentration for pain relief and allow the patient the opportunity to apply needed concentrations to large pain regions of the body, e.g., both feet in a diabetic neuropathy patient, feet, calves and hands/fingers in the diabetic patient or large areas of the chest or back in postherpetic neuralgia patients.

The following examples further illustrate the present invention and are not intended to be limited thereto.

EXAMPLE 1

A kilogram (kg) batch of gel was prepared having the following formula:

| Components | % (w/w) | Gram Amount |
| --- | --- | --- |
| Clonidine Hydrochloride USP | 0.05 | 0.5 |
| Benzyl Alcohol NF | 1 | 10 |
| Carbomer[1] | 0.5 | 5 |
| Sodium Hydroxide NF (10% in water) to pH 8 | q.s. | |
| Purified Water USP to 100% | q.s. | q.s. to 1 Kg |

[1]Carbopol 980 NF, B. F. Goodrich Corporation

An aqueous solution of clonidine was prepared in about 80% of the total water content with stirring agitation employing a propeller-type stirrer (Lightnin mixer) for about five minutes or until homogeneous. While maintaining a stirring vortex, the carbomer was sifted into the vortex of the aqueous clonidine solution and dissolved therein with continuous stirring agitation until a homogenous thin, cloudy liquid dispersion was obtained. The benzyl alcohol was added to the liquid dispersion and stirring agitation maintained for at least ten minutes.

The pH of the mixture was measured and then adjusted and concurrently gelled by adding aqueous sodium hydroxide and mixed for about 15–30 minutes. For this process step, the dispersion was stirred with a paddle stirrer (Hobart mixer). The pH and water content was adjusted as needed for the final gel product.

During processing, the pH value may vary in the range of about 7.8 to about 8.2, and if necessary, aqueous (10%) hydrochloric acid NF can be added to adjust the pH to 8.

The same procedure can be used to prepare a topical gel having 0.1% clonidine.

EXAMPLE 2

A pharmacokinetic study was conducted to compare absorption and other pharmacokinetic characteristics following topical applications of daily doses of 3 mg and 6 mg of clonidine employing a topical gel containing 0.1 weight percent clonidine hydrochloride. The study mimicked the realistic use of topical clonidine gel by a patient with painful diabetic neuropathy of the feet and legs. For this study eight, however, normal (i.e., pain free) volunteer adults with no efficacy outcomes were selected who met the following inclusion criteria.

Inclusion Criteria 1. 18 years of age or older.
2. Systolic blood pressure between 100 and 140 mm Hg; Diastolic blood pressure between 60 and 90 mm Hg; Pulse greater than 50 beats per minuter (BPM).
3. Written informed consent provided at screening.
4. Abstention from caffeine on days of heavy blood sampling (last day of each treatment).

Excluded from the study were adults meeting the following exclusion criteria.

Exclusion Criteria

1. Known allergy or hypersensitivity to clonidine.
2. Presence of altered skin integrity including but not limited to, skin wounds, skin abrasions or any disease state affecting dermal integrity or structure in designated application sites.
3. Known or suspected pregnancy.
4. Abnormal results from screening clinical laboratory testing (hematology, blood chemistry and urinalysis).
5. Administration of any medication by any route within one week of starting study (subjects taking oral contraceptives were allowed to continue this medication), or administration of topical products including, but not limited to creams, ointments, lotions and gels to the designated application site was further restricted to within two days before study entry.
6. History or presence of serious medical conditions.
7. Participation in another investigational drug study or use of any clonidine containing product with the last month.
8. Smoking or illicit drug history.
9. Anemia of any etiology.

The study was designed as an unblinded randomized cross-over regimen in which two dose levels of clonidine (3 mg and 6 mg per day) were compared to assess whether tissue saturation is dose related on the assumption topical clonidine forms a reservoir at non-specific binding sites within the skin. The regimen comprised the following six clinical study periods:

(1) Screening period.

Initial vital signs (blood pressure, pulse, temperature) were taken in the morning.

(2) First Fourteen-Day Topical Clonidine Application Period (Study days 1–14).

On study Day 1 of topical clonidine gel application, vital signs were taken in the morning and blood samples were taken both in the morning and in the afternoon to determine clonidine plasma concentration by Gas Chromatograph/ Mass Spectrum analysis, having clonidine sensitivity of 0.025 ng/ml. On Days 2–13 of topical clonidine gel application, vital signs and blood samples were taken in the morning only. On Day 14, only the morning dose of topical clonidine gel was applied and vital signs and blood samples were taken in the morning. Blood samples were also taken after 2, 4, 6, 8 and 12 hours following the application of this last dose.

(3) First Seven-day Blood Sampling Period (Study days 15–21).

Vital signs and blood samples were taken in the morning.

(4) One week, No-treatment Washout Period (Study days 22–28).

No treatment or clinical work performed.

(5) Second Fourteen-day Topical Clonidine Application With Blood Sampling Period (Study days 29–42).

The clinical procedure of study period (2) was repeated.

(6) Second Seven-day Blood Sampling Period (Study days 43–49).

The clinical procedure of study period (3) was repeated.

Half of the randomized population started the treatment sequence with a 3 mg/day dose during Study Period (2) and then followed with the crossover sequence of the 6 mg/day dose during Study Period (5). The other half of the population started the first treatment with the 6 mg/day dose during Study Period (2) and then followed with the crossover sequence of the 3 mg/day dose during Study Period (5). The following protocol was employed for topical application of clonidine.

Clonidine dose of three mg/day.

One dose of one mg clonidine gel was topically applied to a selected area of the skin on the right lower leg three times a day for a total application of three mg clonidine/day to the same designated skin area for a period of 14 consecutive days, during either Study Period (2) or Study Period (5).

Clonidine dose of six mg/day.

A dose of one mg clonidine gel was applied to a selected area of the right leg three times a day and one mg clonidine gel was applied to the same corresponding selected area on the left leg three times a day for a total administration of 6 mg clonidine/day for 14 consecutive days, during either Study Period (2) or Study Period (5).

The gel was applied and rubbed into the skin. The application site was allowed to dry to the touch following application of the gel before clothing was allowed to contact the treated skin.

Individual tubes of topical gel containing 0.1 weight percent clonidine were supplied for each volunteer. From these tubes, the daily total dose was divided into three portions and applied three times daily approximately every eight hours. The clinical investigator's staff measured, dispensed and observed the application of the morning and afternoon doses and the volunteers measured and applied a bedtime dose.

The actual amount of gel applied for a total dose of 3 mg clonidine/day was found to be a mean value of about 3.1 mg/day and for a total of 6 mg clonidine/day was found to be a mean value of about 6.2 mg/day.

The systemic plasma concentrations seen with topical applications of 3 mg and 6 mg of clonidine per day are shown in FIG. 1. The data summarized in FIG. 1 shows a maximum mean plasma concentration of about 0.2 nanograms/ml at the 6 mg/day dose and about 0.05 nanograms/ml at the 3 mg/day dose. These plasma concentrations are at the bottom or below the range considered as the antihypertensive therapeutic threshold of 0.2 or 0.3 nanograms/ml. No side effects were observed in the eight volunteers who applied the 0.1% formulation at doses of either 3 mg or 6 mg per day for 14 consecutive days.

EXAMPLE 3

Several clinical trials were conducted to determine the blood concentration from topical administration as well as therapeutic effectiveness in patients with sympathetically maintained peripheral neuropathic pain syndromes.

Patients suffering with sympathetically maintained neuropathic pain were selected for two clinical trials, Study A and Study B, conducted to determine the therapeutic effectiveness of a clonidine gel containing 0.1 weight percent clonidine hydrochloride. In Study A, systemic clonidine blood concentration from topical administration was also determined.

In Study A, nine patients were selected who were affected with bilateral lower extremity, painful diabetic neuropathy. In Study B, nine patients were selected who were affected with postherpetic neuralgia on generally irregular bodily areas of the trunk.

The ongoing neuropathic pain intensity was subjectively assessed on a Numeric Graphic Pain Score (NGPS) ranging from zero (0)="No pain" to 10="Pain as bad as it could be." Pain relief was also subjectively ranked on a analog pain relief scale ranging from −1=More pain; zero (0)=No change; 1=Some relief; 2=Moderate relief; and 3=Complete relief. A baseline NGPS value was assessed before starting the trial, and both NGPS and pain relief scores were assessed on each week of the trial following topical application of the topical clonidine gel.

Each dose treatment was a period of seven days. The clonidine gel was applied by the patient to the affected painful region of the patient's body and rubbed into the skin. Sufficient topical gel was applied to provide a predetermined unit dosage amount of clonidine and total milligram (mg) amount of clonidine dose/day. The amount of clonidine dose/day was increased weekly by increasing the number of applications per day as described in the following protocol.

Study A.

Week 1: Sufficient gel to provide a unit dosage amount of about 0.625 mg clonidine per foot was applied twice a day for a total daily dose of 2.5 mg clonidine.

Week 2: Sufficient gel to provide a unit dosage amount of about 0.625 mg clonidine per foot was applied three times a day, at spaced intervals of about 8 hours, to provide a total daily dose of 3.75 mg clonidine.

Week 3: Sufficient gel to provide a unit dosage amount of about 0.625 mg clonidine per foot was applied four times a day, at spaced intervals of about 6 hours, to provide a total daily dose of 5 mg clonidine.

For Study B, the protocol of Study A was repeated, except that each unit dosage amount applied was 0.5 mg clonidine for a total daily dose of clonidine during week 1 of 1 mg; during week 2 of 1.5 mg; and during week 3 of 2 mg.

The individual and average NGPS and pain relief outcome data for Study A and Study B, respectively, are shown in Tables 1 and 2 below.

TABLE 1

STUDY A
Painful Diabetic Neuropathy OutCome Data
(dosing in mg of clonidine/day) Clonidine 0.1% gel

| Patient # | Baseline NGPS | NGPS 2.5 mg | NGPC 3.75 mg | NGPS 5 mg | Pain Relief 2.5 mg | Pain Relief 3.75 mg | Pain Relief 5 mg |
|---|---|---|---|---|---|---|---|
| 1 | 10 | 6 | 3 | 2 | 2 | 1 | 2 |
| 2 | 10 | 5 | 5 | 8 | 1 | 0 | 2 |
| 3 | 8 | 1 | 0 | 0 | 2 | 2 | 2 |
| 4 | 5 | 3 | 7 | 5 | 1 | −1 | 1 |
| 5 | 10 | 5 | 8 | 5 | 0 | 0 | 0 |
| 6 | 8 | 5 | 4 | 4 | 1 | 1 | 1 |
| 7 | 8 | 6 | 5 | 0 | 2 | 1 | 2 |
| 8 | 7 | 8 | 7 | DC | 0 | 1 | DC |

TABLE 1-continued

STUDY A
Painful Diabetic Neuropathy OutCome Data
(dosing in mg of clonidine/day) Clonidine 0.1% gel

| Patient # | Baseline NGPS | NGPS 2.5 mg | NGPC 3.75 mg | NGPS 5 mg | Pain Relief 2.5 mg | Pain Relief 3.75 mg | Pain Relief 5 mg |
|---|---|---|---|---|---|---|---|
| 9 | 4 | 6 | 1 | 1 | 1 | 2 | 2 |
| Average | 7.8 | 4.1 | 4.4 | 3.1 | 1.1 | 0.8 | 1.5 |

NGPS (Numerio Graphic Pain Score) scores ranged from 0, "No Pain" to 10, "Pain as bad as it could be" Pain Relief scores ranged from −1, More pain; 0, No change; 1 Some relief; 2 Moderate relief; and 3 Complete relief DC = Discontinued Eight of the nine patients with bilateral lower extremity, painful diabetic neuropathy, reported decreased pain scores or increased relief scores. The systemic clonidine blood concentration was below the limit of detection (0.025 ng/ml) in all but two of 38 blood samples.

TABLE 2

STUDY B
Postherpetic Neuralgia Outcome Data
(dosing in mg of clonidine/day) Clonidine 0.1% gel

| Patient # | Baseline NGPS | NGPS 1 mg | NGPC 1.5 mg | NGPS 2 mg | Pain Relief 1.0 mg | Pain Relief 1.5 mg | Pain Relief 2 mg |
|---|---|---|---|---|---|---|---|
| 1 | 4 | 2 | 1 | 1 | 2 | 2 | 2 |
| 2 | 7 | 7 | 7 | 6 | 0 | 1 | 1 |
| 3 | 8 | 5 | 3 | 3 | 0 | 1 | 1 |
| 4 | 3 | 2 | 2 | 2 | 1 | 1 | 1 |
| 5 | 3 | 3 | 3 | 4 | 0 | 0 | 1 |
| 6 | 7 | 7 | 5 | 4 | 0 | 1 | 2 |
| 7 | 3 | 2 | 2 | 2 | 1 | 1 | 2 |
| 8 | 7 | 4 | 5 | 10 | 1 | 1 | 1 |
| 9 | 6 | 6 | 4 | 3 | 1 | 1 | 1 |
| Average | 5.3 | 4.2 | 3.5 | 3.9 | 0.7 | 1.0 | 1.3 |

NGPS (Numerio Graphic Pain Score) scores ranged from 0, "No Pain" to 10, "Pain as bad as it could be" Pain Relief scores ranged from −1, More pain; 0, No change; 1 Some relief; 2 Moderate relief; and 3 Complete relief DC = Discontinued Seven of nine patients reported decreased pain scores. All patients reported at least "some relief" at the 2 mg/day dose.

The data show that 15 of 18 patients (83%) were considered clonidine responders. More significantly, the neuropathic pain these patients experienced was refractory to previous interventions.

EXAMPLE 4

The clinical trial procedure of Example 3 (Study A) was repeated, except that ten patients were selected who were affected with bilateral lower extremity, painful diabetic neuropathy and the treatment period was increased to two weeks. The six week trial (Study C) was conducted employing the clonidine gel of Example 1 containing 0.05 weight percent clonidine hydrochloride. The patients applied sufficient topical gel to the affected region to provide a predetermined unit dosage amount of clonidine and the total mg amount of clonidine dose/day was increased every two weeks by changing the number of applications per day as described in the following protocol.

Weeks 1 & 2: Sufficient gel to provide a unit dosage of about 0.31 mg clonidine per foot was applied twice a day to provide a total daily dose of 1.25 mg clonidine.

Weeks 3 & 4: Sufficient gel to provide a unit dosage of about 0.31 mg clonidine per foot was applied three times a day at spaced intervals of about eight hours to provide a total daily dose of 1.875 mg clonidine.

Weeks 5 & 6: Sufficient gel to provide a unit dosage of about 0.31 mg clonidine per foot was applied four times a day at spaced intervals of about six hours to provide a total dose of 2.5 mg clonidine.

The individual and average NGPS and pain relief outcome data are shown in Table 3 below.

TABLE 3

STUDY C
Painful Diabetic Neuropathy Outcome
(dosing in mg of clonidine/day)
Clonidine 0.05% gel

| Patient # | Baseline NGPS | NGPS 1.25 mg | NGPS 1.875 mg | NGPS 2.5 mg | Pain Relief 1.25 mg | Pain Relief 1.875 mg | Pain Relief 2.5 mg |
|---|---|---|---|---|---|---|---|
| 1 | 5 | 5 | 3 | 3 | 1 | 2 | 2 |
| 2 | 6 | 4 | 2 | 4 | 1 | 2 | 2 |
| 3 | 6.5 | 7 | 6 | 6 | 2 | 2 | 2 |
| 4 | 5 | 5 | 3 | 2 | 1 | 2 | 2 |
| 5 | 4 | 3.5 | 2 | 1 | 2 | 2 | 2 |
| 6 | 6 | 5 | 5.5 | 4.5 | 1 | 1 | 2 |
| 7 | 4 | 1.5 | 1 | 2 | 2 | 2 | 2 |
| 8 | 8 | 5 | 5 | 0 | 2 | 2 | 3 |
| 9 | 8 | 7 | 7 | 0 | 2 | 2 | 3 |
| 10 | 3 | 1 | 3 | 0 | 2 | 2 | 3 |
| Average | 5.5 | 4.4 | 3.75 | 2.2 | 1.6 | 1.9 | 2.3 |

NGPS (Numerio Graphic Pain Score) scores ranged from 0, "No Pain" to 10, "Pain as bad as it could be" Pain Relief scores ranged from −1, More pain; 0, No change; 1 Some relief; 2 Moderate relief; and 3 Complete relief DC = Discontinued All ten patients with bilateral, lower extremity, painful diabetic neuropathy reported decreased pain scores and increased relief scores.

I claim:

1. A topical aqueous gel suitable for relieving sympathetically maintained peripheral neuropathic pain syndrome and comprising clonidine, water, and a water-gelling amount of a pharmaceutically acceptable gelling agent selected from the group consisting of carbomers, glycerine polyacrylate, and mixtures thereof, the topical aqueous gel having a physiologically tolerable pH value.

2. The topical aqueous gel in accordance with claim 1 wherein clonidine is present in an amount in the range of about 0.01 to about 0.5 weight percent, based on the weight of the gel.

3. The topical aqueous gel in accordance with claim 1 wherein clonidine is present in an amount in the range of about 0.01 to about 0.25 weight percent, based on the weight of the gel.

4. The topical aqueous gel in accordance with claim 1 wherein clonidine is present in an amount in the range of about 0.01 to about 0.075 weight percent, based on the weight of the gel.

5. The topical aqueous gel in accordance with claim 1 wherein the pH value of the gel is in the range of about 4 to about 9.

6. The topical aqueous gel in accordance with claim 1 wherein the pH value of the gel is in the range of about 6 to about 8.5.

7. The topical aqueous gel in accordance with claim 1 wherein the pH value of the gel is about 8.

8. The topical aqueous gel in accordance with claim 1 further including a preservative.

9. The topical aqueous gel in accordance with claim 8 wherein the preservative is benzyl alcohol.

10. The topical aqueous gel in accordance with claim 8 wherein the preservative is a paraben compound.

11. The topical aqueous gel in accordance with claim 8 wherein the preservative is phenoxyethanol.

12. The topical aqueous gel in accordance with claim 1 further including a topical anaesthetic.

13. The topical aqueous gel in accordance with claim 12 wherein the topical anaesthetic is lidocaine.

14. The topical aqueous gel in accordance with claim 1 wherein the gelling agent is a carbomer.

15. The topical aqueous gel in accordance with claim 14 further including glycerine polyacrylate as a minor portion of the gelling agent.

16. The topical aqueous gel in accordance with claim 1 wherein the gelling agent is glycerine polyacrylate.

17. The topical aqueous gel in accordance with claim 1 further including a skin-humectant adjuvant selected from the group consisting of polyhydric alcohols and polyglycerols.

18. The topical aqueous gel in accordance with claim 1 wherein at least some of the clonidine is present as clonidine hydrochloride.

19. The topical aqueous gel in accordance with claim 1 wherein the clonidine is present as both clonidine hydrochloride and clonidine free base.

20. A method for relieving sympathetically maintained peripheral neuropathic pain syndromes which comprises applying topically to the affected region of a patient suffering from such pain a pain relieving amount of an aqueous gel comprising clonidine, and a water-gelling amount of a pharmaceutically acceptable gelling agent selected from the group consisting of carbomers, glycerine polyacrylate, and mixtures thereof, the topical aqueous gel having a physiologically tolerable pH value.

21. The method in accordance with claim 20 wherein the aqueous gel is applied at least once daily.

22. The method in accordance with claim 20 wherein the aqueous gel is applied two to four times a day.

23. The method in accordance with claim 20 wherein the applied amount of clonidine is in the range of about 0.1 milligram per day to about 6 milligrams per day.

24. The method in accordance with claim 20 wherein after application to the affected region the aqueous gel is rubbed in.

25. The method in accordance with claim 20 wherein the amount of aqueous gel applied is sufficient to produce a blood plasma concentration of clonidine of not more than about 0.2 nanograms per milliliter.

* * * * *